United States Patent [19]

Osman et al.

[11] 4,349,452
[45] Sep. 14, 1982

[54] CYCLOHEXYLCYCLOHEXANOATES

[75] Inventors: Maged A. Osman, Zurich; Laszlo Révész, Fislisbach, both of Switzerland

[73] Assignee: Merck Patent GmbH, Darmstadt, Fed. Rep. of Germany

[21] Appl. No.: 169,135

[22] Filed: Jul. 15, 1980

[30] Foreign Application Priority Data

Jul. 18, 1979 [CH] Switzerland ............ 6672/79

[51] Int. Cl.³ .............. C07C 121/75; C07D 295/14; G02F 1/13; C09K 3/34
[52] U.S. Cl. ............ 252/299.61; 252/299.63; 260/326.4; 260/464; 260/465 D; 546/215; 546/221; 546/223; 546/230; 546/235; 546/239; 560/19; 560/20; 560/45; 560/49; 560/102; 560/107; 560/126; 560/127
[58] Field of Search ............ 252/299, 299.61, 299.63; 546/230, 235, 239, 215, 223, 221; 260/326.4, 465 D, 464; 560/20, 45, 49, 19, 102, 107, 126, 127

[56] References Cited

U.S. PATENT DOCUMENTS

| | | | |
|---|---|---|---|
| 4,013,582 | 3/1977 | Gavrilovic | 252/299 |
| 4,029,595 | 6/1977 | Ross et al. | 560/59 X |
| 4,113,647 | 9/1978 | Coates et al. | 560/65 X |
| 4,130,502 | 12/1978 | Eidenschink et al. | 252/299.63 |
| 4,181,625 | 1/1980 | Eidenschink et al. | 252/299.63 |
| 4,222,887 | 9/1980 | Matsufuji | 252/299 |
| 4,229,315 | 10/1980 | Krause et al. | 560/118 X |
| 4,293,434 | 10/1981 | Deutscher et al. | 252/299.63 |

FOREIGN PATENT DOCUMENTS

| | | | |
|---|---|---|---|
| 23730 | 2/1981 | European Pat. Off. | 252/299.63 |
| 105701 | 5/1974 | German Democratic Rep. | 252/299.63 |

OTHER PUBLICATIONS

Osman M., et al., *Mol. Cryst. Liq. Cryst.*, 56 (Letters), 105-109 (1979).
Deutscher H., et al., "Advances in Liquid Crystal Research and Applications", in *Proc. Third Liq. Cryst. Conf. Socialist Countries*, Budapest 27-31, Aug., 1979, Bata, L. (Editor), Pergamon Press, New York, vol. 2 (1980), pp. 1075-1079.
March, J., *Advanced Organic Chemistry*, McGraw Hill, New York, 1968, pp. 319-320.

*Primary Examiner*—Richard A. Schwartz
*Attorney, Agent, or Firm*—Oblon, Fisher, Spivak, McClelland & Maier

[57] ABSTRACT

Anisotropic compounds of the formula (1)

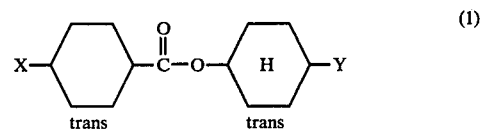

wherein X and Y are each hydrogen, $C_1$-$C_{12}$ alkyl, $C_1$-$C_{12}$ alkoxy, N-monoalkaylamine having 1 to 12 carbon atoms in the alkyl group, halogen, cyano, nitro, or a cyclic radical of the formula

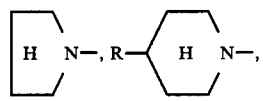

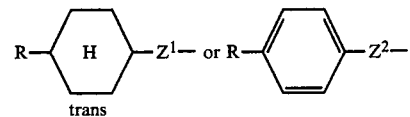

wherein R is hydrogen, halogen, cyano, nitro, $C_1$-$C_{12}$ alkyl, or $C_1$-$C_{12}$ alkoxy, $Z^1$ is a —COO— group or a —OOC— group and $Z^2$ may be the same as $Z^1$ or a single convalent bond, with the proviso that:
  (a) only one of the groups X and Y is a cyclic radical, and
  (b) neither of the groups X or Y is hydrogen, bromine, or poperidino when the other is hydrogen, have low Δn-values without a greay tendency to form smectic phases and are useful in preparing liquid crystal devices.

6 Claims, No Drawings

CYCLOHEXYLCYCLOHEXANOATES

BACKGROUND OF THE INVENTION

1. Field of the Invention

This invention relates to new anisotropic compounds, and more particularly to new classes of cyclohexylcyclohexanoates and liquid crystal (LC) compositions containing these cyclohexylcyclohexanoates which can be used as dielectrics in liquid crystal devices. The invention also relates to a process for preparing the new anisotropic compounds and LC-mixtures containing the new anisotropic compounds.

2. Description of the Prior Art

Anisotropic biphenyl compounds of the formula (10)

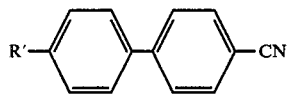

(10)

in which R' represents, for example, an alkyl group, have been disclosed, for example, in German Offenlegungsschrift No. 2,356,085, and are among the materials most often used for LC-mixtures.

It is also known from German Offenlegungsschrift No. 2,636,684 that the comparatively high viscosity and high Δn-values of the compounds of formula (10) can be decreased by replacing one of the phenylene rings by a trans-1,4-cyclohexylene ring. Such compounds are phenylcyclohexanes of the formula (20).

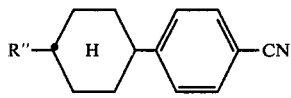

(20)

in which R'' has the same significance as R' in formula (10).

The Δn-values of anisotropic components of LC-mixtures are commonly used as a measure of the optical anisotropy and are calculated as the difference between the refractive indices parallel and perpendicular to the molecular axis of the particular material, that is, $\Delta n = n_{\|} - n_{\perp}$.

For many types of LC-devices, especially the so-called "guest-host" effect cells, nematic LC-phases with the smallest possible Δn-values, i.e., not greater than 0.1, are required. By replacement of one of the phenylene rings in the compounds of formula (10) by a trans-cyclohexylene ring the Δn-value is decreased by nearly half ($\Delta n \approx 0.22$ in compounds of formula (10). $\Delta n \approx 0.12$ in compounds of formula (20)).

If the second phenylene ring of the anisotropic compounds of the formula (10), that is the remaining phenylene ring of the compounds of formula (20), is replaced by a cyclohexylene ring, the cyclohexylcyclohexanes of the formula (30)

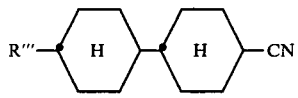

(30)

are obtained in which R''' has the same significance as R' in formula (10). These compounds ae disclosed in German Offenlegungsschrift No. 2,702,598. In these compounds the Δn-value is further decreased and, indeed, is less than 0.1, typically about 0.06.

However, the compounds of the formula (30) have the drawback (see R. Pohl et al., Phys. Letter 65A (2), 169(1978)) that the hydrogenation of the second phenylene ring produces a marked tendency toward the formation of smectic phases.

Therefore a need has continued to exist for LC-compounds having a low Δn-value combined with a low tendency for formation of smectic phases.

SUMMARY OF THE INVENTION

Accordingly, it is an object of the invention to provide new anisotropic compounds suitable for use in LC-devices.

A further object of the invention is to provide new anisotropic compounds which have a low Δn-value, preferably less than 0.1.

A further object of the invention is to provide new anisotropic compounds which do not have a pronounced tendency to form smectic phases.

Further object of the invention will be apparent from the description of the invention which follows.

It has now been found that the objects of the invention can be attained when the planarity of the molecule having two neighboring cyclohexane rings is interrupted by the interposition of a carboxyl group. It has also been found that this structural alteration does not destroy the anisotropy of the molecule.

The new anisotropic compounds of the invention have the formula (1)

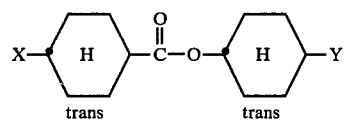

(1)

in which X and Y independently signify hydrogen, $C_1$–$C_{12}$ alkyl groups, $C_1$–$C_{12}$ alkoxy groups, N-monoalkylamino groups having 1 to 12 carbon atoms in the alkyl group, halogen, cyano, or nitro, and one of the groups X or Y can additionally be a cyclic radical of the formula

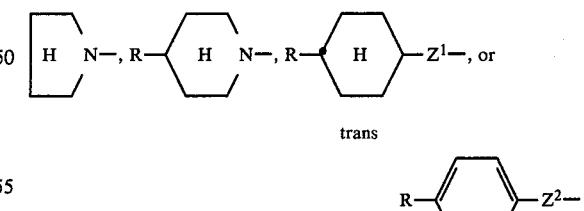

in which R is halogen, cyano, nitro, or an alkyl or alkoxy group having 1 to 12 carbon atoms, $Z^1$ represents the —COO— group or —OOC— group and $Z^2$ may be the same as $Z^1$ or a single covalent bond. However, only one of the X or Y groups can be a cyclic radical, and neither of the X or Y groups can be hydrogen when the other is hydrogen, bromine or piperidino.

The new anisotropic compounds (1) are distinguished from the known cyclohexane carboxylic acid phenyl esters of German Offenlegungsschrift No. 2,429,093, not only by reason of their structure but also by their technical utility, and especially their ΔN-values.

DETAILED DESCRIPTION OF THE INVENTION AND PREFERRED EMBODIMENTS

The new compounds can be prepared by condensing the corresponding cyclohexanecarboxylic acid of the formula (2)

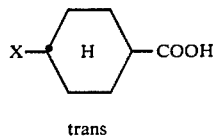

(2)

preferably after conversion into the corresponding acid halide, with the corresponding cyclohexanol of formula (3)

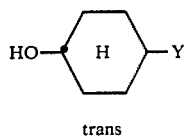

(3)

to prepare the desired compound (1). Suitable cyclohexanecarboxylic acids (2) and cyclohexanols (3) are known and/or can be prepared by known procedures. For example, the compounds of formula (2) can be prepared by hydrogenation of the corresponding benzoic acid compounds.

When X or Y in the formula (1), (2), and (3) is not hydrogen, the trans-form of the corresponding compound is always meant as is indicated in the formulas by a dot in the usual manner. When mixtures of cis- and trans-isomers arise in the preparation of the starting compounds (2) and (3), the desired trans-isomers can be obtained in the usual manner by fractional crystallization or other similar methods.

Preferably the cyclohexanecarboxylic acid compounds of formula (2) are converted by reaction with $SO_2Cl$ into the corresponding acid halides of the formula (2')

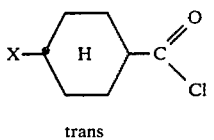

(2')

and these are in turn condensed with the cyclohexanol compounds of formula (3) in the presence of a normally liquid organic base, which preferably also serves as the reaction medium, for example, pyridine.

The new compounds of formula (1) according to the invention are anisotropic, that is, they exhibit either enantiotropic liquid crystal properties or monotropic liquid crystal properties. In monotropically liquid crystalline materials the clear point ($T_c$) of the pure substance is lower than its melting point ($T_m$). However, it can be measured by supercooling of the pure monotropic substance or can be determined by studying an enantiotropic mixture containing the monotropic substance and calculating the mesomorphic contribution of the monotropic substance. Surprisingly, the new anisotropic compounds of formula (1) exhibit practically no pronounced tendency to form smectic phases. Because of the properties of the cyclohexyl ester described by R. Eidenschink et al. (Eighth Freibourg Workshop, 1978) which had very broad smectic phase range, it was all the more to be expected that a carboxyl group positioned between two cyclohexane rings would have no significant influence on the pronounced tendency of the cyclohexylcyclohexanes (30) to form smectic mesophases.

On the other hand, the carboxyl group used as the bridge between neighboring cyclohexane rings in the new anisotropic compounds (1) of the invention plainly has no effect on the optical anisotropy, since the compounds of the invention have an Δn-value of less than 0.1 and offer corresponding advantages when used as components of LC-mixtures.

It will be evident to one skilled in the art from the above explanation that the new anisotropic compounds of formula (1) have an extraordinary broad range of applications. According to the choice of the substituents X and Y, in formula (1) to produce a stronger or weaker polarization of the molecule, the new anisotropic compounds can perform different functions in LC-mixtures for LC-devices of different types. The anisotropic compounds of formula (1) can be used either alone or in mixture. Widely differing mixtures can be prepared which are comprised predominantly or practically entirely (e.g., up to 90% by weight) of the new anisotropic compounds (1) or contain these compounds only as components (e.g., in proportions of 2 to 40% by weight). The preferred halogens for X, Y, and R are generally chlorine and bromine.

Having generally described the invention, a more complete understanding can be obtained by reference to certain specific examples, which are provided herein for purposes of illustration only and are not intended to be limiting unless otherwise specified. In the following examples the percentages given are percentages by weight. Unless otherwise specified, the cyclohexane compounds used as starting materials are in the trans-configuration. All compounds of the invention prepared in the examples have the trans-configuration.

EXAMPLE 1

Preparation of 4-methylcyclohexyl-4'-pentylcyclohexanoate (Formula 1: $X=C_5H_{11}$, $Y=CH_3$)

A quantity of 2.1 g (10.6 mMol) of 4-n-pentylcyclohexanecarboxylic acid (Formula 2: $X=C_5H_{11}$) was heated to reflux temperature in 10 ml of thionyl chloride for 20 minutes. The mixture was then concentrated, and the thionyl chloride was completely driven off by thrice adding 20 ml portions of toluene and again concentrating. The acid chloride so obtained was mixed with 12 ml of pyridine and reacted with 1.2 g (106 mMol) of 4-methylcyclohexane in 6 ml of pyridine with stirring. The reaction mixture was stirred for two hours at room temperature and for 30 minutes at 60° C., then poured into ice-cold 2 N HCl, and extracted three times with methylene chloride. The organic phase was washed once with ice-cold 2 N NaOH, and once with a NaCl solution, then concentrated to yield 3.0 g of bright yellow crystals. After recrystallization from ethanol and hexane the pure desired compound was obtained in the form of colorless crystals (GC 99.7%) $T_m$ 18.3° C., $T_c$ 3.3° C.

EXAMPLES 2–74

By the procedure of Example 1 using the correspondingly substituted cyclohexanecarboxylic acids of formula (2) and the correspondingly substituted cyclohexanols of formula (3) the following compounds of formula (1) were prepared.

(2) 4-Propylcyclohexyl-4'-propylcyclohexanoate
(3) 4-Propylcyclohexyl-4'-pentylcyclohexanoate
(4) 4-Propylcyclohexyl-4'-heptylcyclohexanoate
(5) 4-Pentycyclohexyl-4'-propylcyclohexanoate
(6) 4-Pentylcyclohexyl-4'-pentylcyclohexanoate
(7) 4-Propyloxycyclohexyl-4'-propylcyclohexanoate
(8) 4-Propyloxycyclohexyl-4'-pentylcyclohexanoate
(9) 4-Propyloxycyclohexyl-4'-heptycyclohexanoate
(10) 4-Pentyloxycyclohexyl-4'-propylcyclohexanoate
(11) 4-Pentyloxycyclohexyl-4'-pentylcyclohexanoate
(12) 4-Propylcyclohexyl-4'-propyloxycyclohexanoate
(13) 4-Propylcyclohexyl-4'-pentyloxycyclohexanoate
(14) 4-Propylcyclohexyl-4'-heptyloxycyclohexanoate
(15) 4-Pentylcyclohexyl-4'-propyloxycyclohexanoate
(16) 4-Pentylcyclohexyl-4'-pentyloxycyclohexanoate
(17) 4-Propyloxycyclohexyl-4'-propyloxycyclohexanoate
(18) 4-Propyloxycyclohexyl-4'-pentyloxycyclohexanoate
(19) 4-Propyloxycyclohexyl-4'-heptyloxycyclohexanoate
(20) 4-Pentyloxycyclohexyl-4'-propyloxycyclohexanoate
(21) 4-Pentyloxycyclohexyl-4'-pentyloxycyclohexanoate
(22) 4-Pyrrolidinocyclohexyl-4'-nonylcyclohexanoate
(23) 4-Propylcyclohexyl-4'-cyanocyclohexanoate
(24) 4-Butylcyclohexyl-4'-cyanocyclohexanoate
(25) 4-Pentylcyclohexyl-4'-cyanocyclohexanoate
(26) 4-Nonylcyclohexyl-4'-cyanocyclohexanoate
(27) 4-Propylcyclohexyl-4'-nitrocyclohexanoate
(28) 4-Pentylcyclohexyl-4'-nitrocyclohexanoate
(29) 4-Nonylcyclohexyl-4'-nitrocyclohexanoate
(30) 4-Propylcyclohexyl-4'-chlorocyclohexanoate
(31) 4-Pentylcyclohexyl-4'-chlorocyclohexanoate
(32) 4-Nonylcyclohexyl-4'-chlorocyclohexanoate
(33) 4-Propylcyclohexyl-4'-bromocyclohexanoate
(34) 4-Pentylcyclohexyl-4'-bromocyclohexanoate
(35) 4-Nonylcyclohexyl-4'-bromocyclohexanoate
(36) 4-Cyanocyclohexyl-4'-propylcyclohexanoate
(37) 4-Cyanocyclohexyl-4'-pentylcyclohexanoate
(38) 4-Cyanocyclohexyl-4'-nonylcyclohexanoate
(39) 4-Nitrocyclohexyl-4'-propylcyclohexanoate
(40) 4-Nitrocyclohexyl-4'-pentylcyclohexanoate
(41) 4-Nitrocyclohexyl-4'-nonylcyclohexanoate
(42) 4-Chlorocyclohexyl-4'-propylcyclohexanoate
(43) 4-Chlorocyclohexyl-4'-pentylcyclohexanoate
(44) 4-Chlorocyclohexyl-4'-nonylcyclohexanoate
(45) 4-Bromocyclohexyl-4'-propylcyclohexanoate
(46) 4-Bromocyclohexyl-4'-pentylcyclohexanoate
(47) 4-Bromocyclohexyl-4'-nonylcyclohexanoate
(48) 4-Propylcyclohexyl-4'-butylaminocyclohexanoate
(49) 4-Propylcyclohexyl-4'-hexylaminocyclohexanoate
(50) 4-Pentylcyclohexyl-4'-butylaminocyclohexanoate
(51) 4-Pentylcyclohexyl-4'-hexylaminocyclohexanoate
(52) 4-Cyanocyclohexyl-4'-butylaminocyclohexanoate
(53) 4-Cyanocyclohexyl-4'-hexylaminocyclohexanoate
(54) 4-Nitrocyclohexyl-4'-butylaminocyclohexanoate
(55) 4-Nitrocyclohexyl-4'-hexylaminocyclohexanoate
(56) 4-Bromocyclohexyl-4'-butylaminocyclohexanoate
(57) 4-Bromocyclohexyl-4'-hexylaminocyclohexanoate
(58) 4-Cyanocyclohexyl-4'-pyrrolidinocyclohexanoate
(59) 4-Nitrocyclohexyl-4'-pyrrolidinocyclohexanoate
(60) 4-Bromocyclohexyl-4'-pyrrolidinocyclohexanoate
(61) 4-Propylcyclohexyl-4'-pyrrolidinocyclohexanoate
(62) 4-Pentylcyclohexyl-4'-pyrrolidinocyclohexanoate
(63) 4-Heptylcyclohexyl-4'-pyrrolidinocyclohexanoate
(64) 4-Butylaminocyclohexyl-4'-cyanocyclohexanoate
(65) 4-Butylaminocyclohexyl-4'-nitrocyclohexanoate
(66) 4-Butylaminocyclohexyl-4'-bromocyclohexanoate
(67) 4-Hexylaminocyclohexyl-4'-cyanocyclohexanoate
(68) 4-Hexylaminocyclohexyl-4'-bromocyclohexanoate
(69) 4-Hexylaminocyclohexyl-4'-nitrocyclohexanoate
(70) 4-Pyrrolidinocyclohexyl-4'-cyanocyclohexanoate
(71) 4-Pyrrolidinocyclohexyl-4'-nitrocyclohexanoate
(72) 4-Pyrrolidinocyclohexyl-4'-bromocyclohexanoate
(73) 4-Pyrrolidinocyclohexyl-4'-propylcyclohexanoate
(74) 4-Pyrrolidinocyclohexyl-4'-pentylcyclohexanoate All the listed compounds had the trans-configuration.

EXAMPLE 75

Preparation of 4-phenylcyclohexyl-4-propylcyclohexanoate (Formula 1: X=n—$C_3H_7$, Y=phenyl)

A quantity of 2.2 g (13 mMol) of n-propylcyclohexancarboxylic acid (Formula 2: X=n—$C_3H_7$) was heated to reflux temperature in 10 ml of thionyl chloride for two hours. The mixture was then concentrated, and all traces of thionyl chloride were eliminated by twice adding 20 ml portions of benzene and again concentrating. A quantity of 2.2 g (12.5 mMol) of 4-phenylcyclohexanol (Formula 3: Y=phenyl) was dissolved in 20 ml of pyridine at room temperature and added dropwise to a solution of the acid chloride in 10 ml of pyridine while cooling. The reaction mixture was stirred for 5 hours at room temperature, then poured into ice-cold 2 N HCl and extracted three times with ether. The ether extract was washed once with ice cold 2 N NaOH, and once with a NaCl solution, then dried over $Na_2SO_4$ and concentrated. The crude product was obtained as 3.6 g of yellow crystals. After three recrystallizations from ethanol the desired product was obtained in the form of colorless crystals (GC 99.8%), $T_m$ 84.4° C., $T_c$ 69.5° C.

EXAMPLES 76–96

By the procedure described in Example 75 the following compounds of formula (1) were prepared in analogous manner. All the compounds were in the trans-configuration.

(76) 4-Propylcyclohexyl-(4''-propylpiperidino-4')-cyclohexanoate
(77) 4-Pentylcyclohexyl-(4''-propylpiperidino-4')-cyclohexanoate
(78) 4-Nonylcyclohexyl-(4''-propylpiperidino-4')-cyclohexanoate
(79) 4-Cyanocyclohexyl-(4''-propylpiperidino-4')-cyclohexanoate
(80) 4-Nitrocyclohexyl-(4''-propylpiperidino-4')-cyclohexanoate
(81) 4-Bromocyclohexyl-(4''-propylpiperidino-4')-cyclohexanoate
(82) 4-Propylcyclohexyl-(4''-propyl-p-phenylen-4')-cyclohexanoate
(83) 4-Propylcyclohexyl-(4''-pentyl-p-phenylen-4')-cyclohexanoate

(84) 4-Propylcyclohexyl-(4''-cyano-p-phenylen-4')-cyclohexanoate
(85) 4-Propylcyclohexyl-(4''-bromo-p-phenylen-4')-cyclohexanoate
(86) 4-Propylcyclohexyl-(4''-nitro-p-phenylen-4')-cyclohexanoate
(87) (4''-Propyl-p-phenylen-4')-cyclohexyl-4-propylcyclohexanoate
(88) (4''-Pentyl-p-phenylen-4')-cyclohexyl-4-propylcyclohexanoate
(89) (4''-Cyano-p-phenylen-4')-cyclohexyl-4-propylcyclohexanoate
(90) (4''-Nitro-p-phenylen-4')-cyclohexyl-4-propylcyclohexanoate
(91) (4''-Bromo-p-phenylen-4')-cyclohexyl-4-propylcyclohexanoate
(92) (4''-Propyl-p-phenylen-4')-cyclohexyl-4-pentylcyclohexanoate
(93) (4''-Pentyl-p-phenylen-4')-cyclohexyl-4-pentylcyclohexanoate
(94) (4''-Cyano-p-phenylen-4')-cyclohexyl-4-pentylcyclohexanoate
(95) (4''-Nitro-p-phenylen-4')-cyclohexyl-4-pentylcyclohexanoate
(96) (4''-Bromo-p-phenylen-4')-cyclohexyl-4-pentylcyclohexanoate

EXAMPLES 97–107

Table 1, which follows, gives the usual values of the pertinent properties of several more compounds of the invention characterized by the X and Y groups which are listed in the table. A few of the compounds prepared above are also included in the table. The numbers in the spaces between "C" (crystalline), "S" (smectic), "N" (nematic), and "I" (isotropic) are the temperatures in °C. of the transitions.

TABLE 1

| Example No. | X | Y | K | S | N | I |
|---|---|---|---|---|---|---|
| 97 | CH$_3$ | CH$_3$ | .35.0 | | | . |
| 98 | CH$_3$ | C$_3$H$_7$ | .19.9 | | .(−18.2) | . |
| 99 | CH$_3$ | C$_5$H$_{11}$ | .17.8 | .20.0 | | . |
| 100 | C$_2$H$_5$ | C$_3$H$_7$ | .14.0 | .(−14.2) | .(5.5) | . |
| 101 | C$_3$H$_7$ | CH$_3$ | .21.0 | | | . |
| 102 | C$_3$H$_7$ | C$_2$H$_5$ | .9.1 | | .(−2.6) | . |
| 2 | C$_3$H$_7$ | C$_3$H$_7$ | .22.8 | | .36.6 | . |
| 103 | C$_4$H$_9$ | CH$_3$ | .13.1 | | .(−15.0) | . |
| 104 | C$_5$H$_{11}$ | CH$_3$ | .18.3 | | .(3.3) | . |
| 3 | C$_5$H$_{11}$ | C$_3$H$_7$ | .25.1 | .36.8 | .52.1 | . |
| 37 | C$_5$H$_{11}$ | CN | .59.8 | | (16*) | . |
| 105 | C$_5$H$_{11}$–⟨H⟩– | CH$_3$ | .150.7 | .(150.2) | .155.9 | . |
| 106 | C$_3$H$_7$ | –⟨⟩– | .84.4 | | .(69.5) | . |
| 89 | C$_3$H$_7$ | –⟨⟩–CN | .103.0 | | .206.1 | . |
| 94 | C$_5$H$_{11}$ | –⟨⟩–CN | .94.2 | | .201.3 | . |
| 107 | C$_7$H$_{15}$ | –⟨⟩–CN | .104.6 | | .189.2 | . |
| 84 | C$_5$H$_{11}$–⟨H⟩– | C$_3$H$_7$ | .84.2 | .88.6 | .177.3 | . |

*Determined by extrapolation

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An anisotropic compound having the formula $$X-\underset{trans}{\langle H \rangle}-\overset{\overset{O}{\|}}{C}-O-\underset{trans}{\langle H \rangle}-Y$$

wherein X and Y are each selected from the group consisting of hydrogen, N-monoalkylamino having 1 to 12 carbon atoms in the alkyl portion, halo, cyano, nitro, and cyclic radicals selected from the group consisting of radicals having the following formulas:

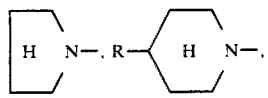

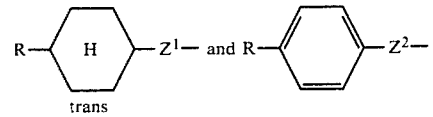

wherein R is selected from the group consisting of halogen, cyano and nitro, $Z^1$ is a carboxyl radical selected from the group consisting of —COO— and —OOC—, and $Z^2$ is selected from the group consisting of $Z^1$ and a single covalent bond, with the proviso that:
(a) only one of the groups X and Y is a cyclic radical, and;
(b) neither of the groups X and Y is hydrogen, bromine, or piperidino when the other is hydrogen.

2. An anisotropic compound having the formula

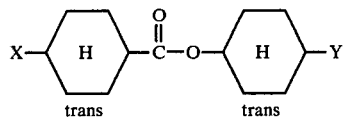

wherein X and Y are each selected from the group consisting of hydrogen, $C_1$–$C_{12}$ alkyl, $C_1$–$C_{12}$ alkoxy, N-monoalkylamino having 1 to 12 carbon atoms in the alkyl portion, halo, cyano and nitro, with the proviso that neither of the groups X and Y is hydrogen or bromine, when the other is hydrogen.

3. An anisotropic compound having the formula

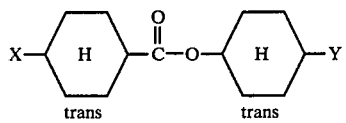

wherein X and Y are each selected from the group consisting of hydrogen, $C_1$–$C_{12}$ alkyl, $C_1$–$C_{12}$ alkoxy, N-monoalkylamino having 1 to 12 carbon atoms in the alkyl portion, halo, cyano, nitro, and cyclic radical selected from the group consisting of radicals having the following formulas:

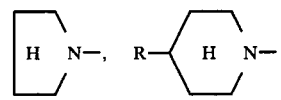

wherein R is selected from the group consisting of halogen, cyano, nitro, $C_1$–$C_{12}$ alkyl, and $C_1$–$C_{12}$ alkoxy with the proviso that:
(a) one and only one of the groups X and Y is a cyclic radical, and;
(b) neither of the groups X and Y is piperidino when the other is hydrogen.

4. An anisotropic compound having the formula

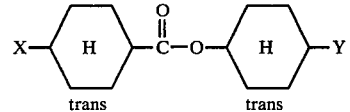

wherein X and Y are each selected from the group consisting of hydrogen, $C_1$–$C_{12}$ alkyl, $C_1$–$C_{12}$ alkoxy, N-monoalkylamino having 1 to 12 carbon atoms in the alkyl portion, halo, cyano, nitro, and cyclic radicals selected from the group consisting of radicals having the following formulas:

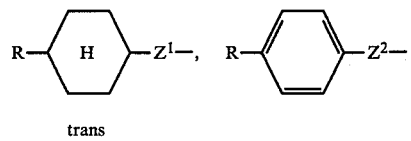

wherein R is selected from the group consisting of halogen, cyano, nitro, $C_1$–$C_{12}$ alkyl, and $C_1$–$C_{12}$ alkoxy and $Z^1$ and $Z^2$ are carboxyl radicals selected from the group consisting of —COO— and —OOC—, with the proviso that one and only one of the groups X and Y is a cyclic radical.

5. An anisotropic compound of the formula

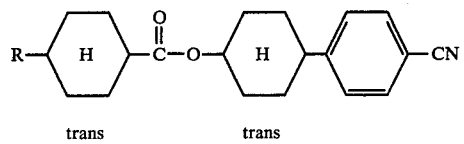

wherein R is $C_1$–$C_{12}$-alkyl.

6. A liquid crystal mixture containing at least one anisotropic compound of claim 1.

* * * * *